United States Patent [19]

Reynolds et al.

[11] 4,023,563

[45] May 17, 1977

[54] APPARATUS AND METHOD FOR DETERMINING ONSET TIMES OF PULSES AND USE THEREOF IN COMPUTING INTERARTERIAL BLOOD PRESSURE ELECTROMECHANICAL INTERVAL

[75] Inventors: Charles A. Reynolds, West Haven; Richard A. Mentelos, Hamden, both of Conn.; Donald E. Lewis, San Gabriel, Calif.

[73] Assignee: American Home Products Corporation, New York, N.Y.

[22] Filed: Sept. 22, 1975

[21] Appl. No.: 615,305

[52] U.S. Cl. .................. 128/2.05 R; 128/2.06 R
[51] Int. Cl.² .................................... A61B 5/02
[58] Field of Search ............ 128/2.05 A, 2.05 D, 128/2.05 F, 2.05 M, 2.05 P, 2.05 Q, 2.05 R, 2.06 R; 73/194 E; 307/235 A, 235 J; 324/188; 328/114, 162

[56] References Cited

UNITED STATES PATENTS

| 3,290,590 | 12/1966 | Baker | 324/188 |
|---|---|---|---|
| 3,334,298 | 8/1967 | Monrad-Krohn | 328/114 |
| 3,708,753 | 1/1973 | Radecke | 328/162 |
| 3,734,086 | 5/1973 | Phelps, Sr. | 128/2.05 P |
| 3,850,169 | 11/1974 | Gebben et al. | 128/2.05 P |

FOREIGN PATENTS OR APPLICATIONS

| 1,083,441 | 9/1967 | United Kingdom | 328/114 |

*Primary Examiner*—William E. Kamm
*Attorney, Agent, or Firm*—Darby & Darby

[57] ABSTRACT

Apparatus and a method for determining the onset of an interarterial blood pressure pulse and measuring the time delay preceding the onset from the corresponding electrical heartbeat triggering signal wherein the blood pressure pulse is converted to an electrical input signal which is split into two identical components, one being delayed in time, inverted and amplified after which it is added to the other. A timer measures the duration between the electrical heartbeat actuating signal and the point at which the sum of the blood pressure component signals reaches a peak and subtracts from that result the time delay applied to the one component to yield the electromechanical interval between the electrical heartbeat signal and onset of the blood pressure pulse.

17 Claims, 12 Drawing Figures

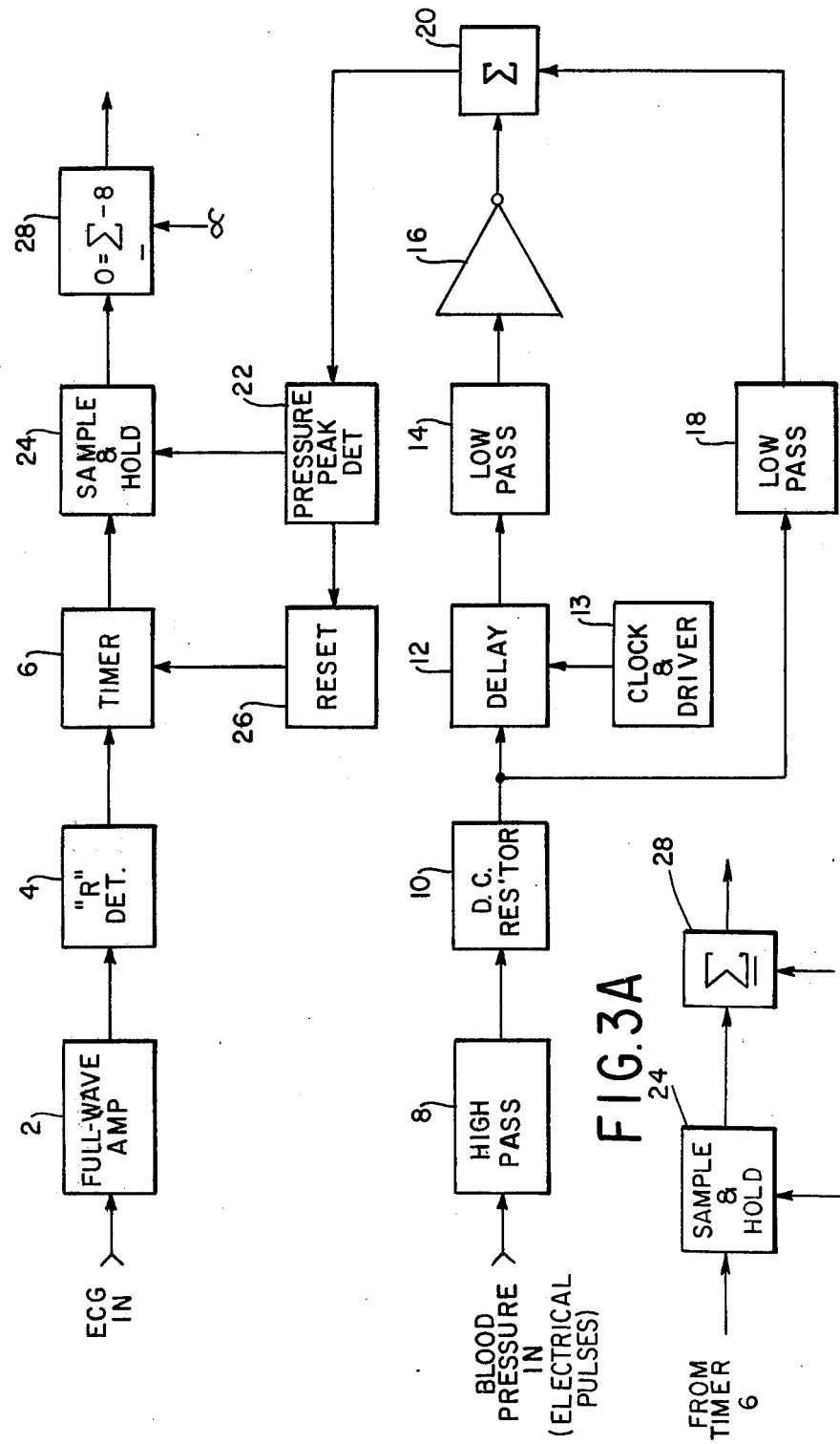

APPARATUS AND METHOD FOR DETERMINING ONSET TIMES OF PULSES AND USE THEREOF IN COMPUTING INTERARTERIAL BLOOD PRESSURE ELECTROMECHANICAL INTERVAL

BACKGROUND OF THE INVENTION

It is known that certain functions of living organisms and also of electrical and mechanical apparatus, are characterized by events which occur in specific time sequences and that the time relationships among such events are indicative of the satisfactory performance of the functions. Thus, by comparing the times between occurrence of two events characteristic of a function with a statistically normal time for the duration between such events it can be determined whether the function is being properly performed. If the measured time deviates from the normal time, diagnosis as to the cause of malfunction may be made.

One of the many possible areas in which event interval measurement may be employed for monitoring and diagnosis is in the care of the newborn infant. It has been found that electromechanical interval is an excellent indicator of neonatal distress. The electromechanical interval is the time between the myocardial electrical impulse (ECG) transmitted to the neonatal heart, commonly shown on the electrocardiogram, and the onset of the absolute blood pressure pulse resulting from the heartbeat. Although the electrical heart signal causes no problem for detection, this is not true of the blood pressure signal. The blood pressure signal is characteristically a noisy one subject to variations in amplitude and onset slope. It is also affected by variations in the blood pressure base line, i.e., the average blood pressure. Thus, in order to accurately measure the electromechanical interval a method for determining blood pressure pulse onset and apparatus necessary for execution of the method are required.

SUMMARY OF THE INVENTION

The above-mentioned problems are overcome by the method and apparatus of this invention for detecting interarterial blood pressure onset. The invention relates to apparatus and a method for determining the time of blood pressure onset irrespective of variations in absolute blood pressure pulse amplitude and slope by measuring the elapsed time from the electrocardiogram representative of the electrical heartbeat actuating signal to blood pressure pulse onset. More specifically, the invention includes electrical circuitry for splitting an electrical signal representative of the blood pressure pulse into two components, delaying, inverting and amplifying one of the components, and then recombining the delayed, inverted, and amplified component with the unaltered component, the sum of the two components having a peak at a point in time equal to the sum of the time of actual onset of the blood pressure pulse measured from the R-wave of the ECG and the delay period applied to the amplified blood pressure pulse component. To determine the actual time of onset, the delay period is subtracted from the time at which the component sum peaks, the result being the electromechanical interval of the neonate.

It is therefore an object of the invention to provide apparatus and a method for determining the onset times of pulses having varying amplitudes and slopes.

Another object of the invention is to provide apparatus and a method for determining the onset of the mechanical blood pressure pulse in a neonate.

Still another object of the invention is to provide a method and apparatus for determining the time interval between two events at least one of which is indicated by the onset of a pulse having varying amplitude and slope characteristics.

A further object of the invention is to provide apparatus and a method for measuring electromechanical interval in a neonate.

Other and further objects of the invention will be apparent from the drawings and description of a preferred embodiment in which like reference designations are used to indicate like characteristics and parts in the various views.

DESCRIPTION OF THE DRAWINGS

FIG. 3 is a flow diagram of the apparatus used to determine electromechanical interval.

FIG. 3A is a flow diagram which illustrates how a polarity detector may be substituted for the peak detector of FIG. 3.

DESCRIPTION OF THE PREFERRED EMBODIMENT

Figure 1A:
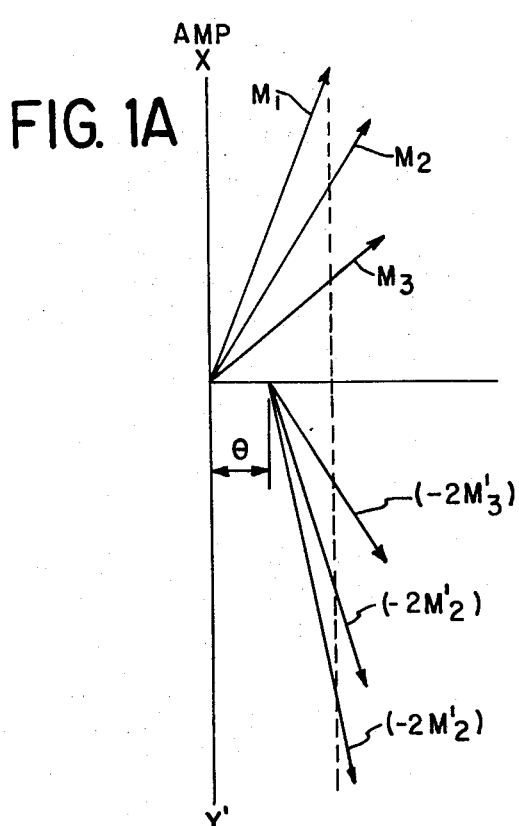
FIG. 1A is a plot of the slopes of three different unaltered pulses and the slopes of said pulses delayed in time, inverted and amplified by a gain of 2.
Figure 1B:
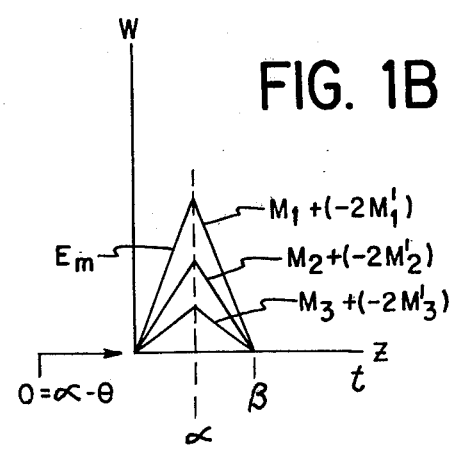
FIG. 1B is a plot of the sum of the unaltered pulse slopes of FIG. 1A and their delayed and amplified counterparts.

Referring to FIG. 1A of the drawings, arrows M1, M2 and M3 represent the slopes of three pulses each having an onset at time zero, i.e., at the origin, and each having a slope differing from that of the others. Arrows M1', M2' and M3' are derived by shifting the onset point 0 along the time axis T a distance of $\theta$ time units and multiplying the slopes of arrows M1, M2, and M3 by a constant, −2. The result of summing M1 and M1', M2 and M2', and M3 and M3' is shown in FIG. 1B. The distance $\alpha$ from the origin, along the time axis, to the peak of each of the summation plots is the same [i.e., $\alpha$]. Thus it can be seen that the time at which the summation reaches its peak is independent of the slopes and amplitudes of the individual pulses. The time delayed pulse components M1', M2' and M3' may be inverted and amplified at a gain having any magnitude greater than one to cause the peaking effect and a gain of 2 is chosen merely as a matter of convenience.

The peak of the summation pressure pulse provides an easily detectable point from which to compute pressure pulse onset. However, the peak of the summation pulse is not the only point from which onset may be computed and there are other characteristics of the summation wave from which lend themselves to onset computation. For example, the point β at which the summation waveform crosses the time axis changing from a positive to a negative value is also independent of the slopes and amplitudes of the individual pulses and may serve as an easily detectable point from which to compute pressure pulse onset with circuitry known to the art.

The method by which electromechanical interval is measured will now be described. Electromechanical interval (EMI) is defined as the time from the peak of the R wave of the electrocardiogram (ECG), shown in FIG. 2a, to the onset of the blood pressure pulse which results from the heartbeat associated with the R wave.

Figure 2A:
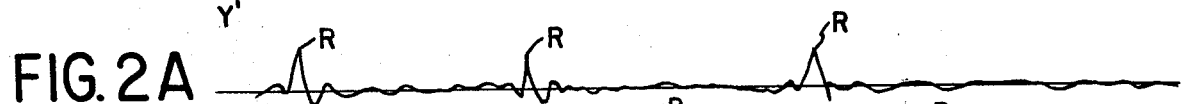
FIG. 2A is a plot of the neonatal electrocardiogram complex as a function of time.
Figure 2B:
FIG. 2B is a plot of absolute neonatal blood pressure as a function of time.
Figure 2C:
FIG. 2C is a plot of neonatal blood pressure as shown in FIG. 2B delayed by a constant time period $\theta$, inverted and amplified by a gain of 2.
Figure 2D:
FIG. 2D is a plot showing the sum of the plots of FIGS. 2B and 2C.

FIG. 2B shows a plot of blood pressure versus time, each of the blood pressure pulses having an onset 0 followed by a peak P and then diminishing again until onset of the following blood pressure pulse. If the pulse train of FIG. 2B is delayed by a time $\theta$, inverted and amplified by a gain of 2, the waveform shown in FIG. 2C results. A summation waveform, shown in FIG. 2D, is derived by adding the original blood pressure pulse waveform of FIG. 2B to the time delayed, inverted and amplified waveform of FIG. 2C. If the delay time $\theta$ is maintained at a constant value below the time necessary for each blood pressure pulse to reach its peak, the peaks $P_s$ of the summation waveform of FIG. 2D will correspond to the onset points 0 of the blood pressure pulses delayed by time $\theta$. In the preferred embodiment of the invention, the time delay $\theta$ is maintained at 18 milliseconds.

The electromechanical interval (EMI) may be measured by a conventional timer which is started in response to the peak of each R wave of the electrocardiogram complex and stopped in response to the peak $P_s$, the zero intercept or any other predetermined detectable characteristic of the summation waveform derived from the blood pressure pulse immediately following the R wave. In the preferred embodiment of the invention the peak of the summation waveform is detected. To correct for the offset of the peak of the summation waveform from the actual onset of the blood pressure pulse, the time delay period $\theta$ is subtracted from the measured interval between the ECG and blood pressure summation peaks, the result being the electromechanical interval.

Figure 2E:
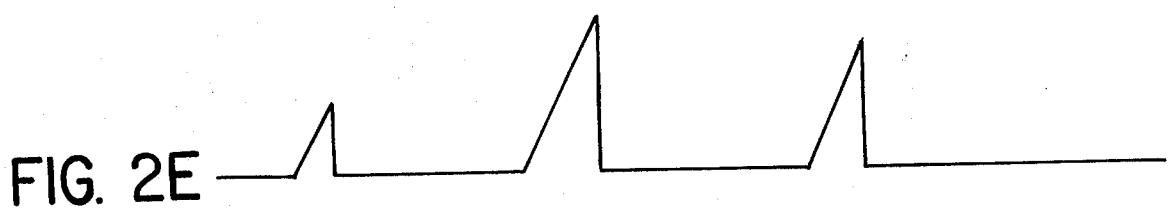
FIG. 2E is a plot of timer voltage as a function of time during measurement of the electromechanical interval.

The electromechanical interval measurement may be accomplished by a novel combination of conventional components functionally arranged as shown in FIG. 3. The electrocardiogram complex illustrated in FIG. 2A is applied to a full wave amplifier 2 which provides at its output a waveform of consistent polarity. The full wave amplified ECG is then applied to a peak detector 4 to detect the peak of the R wave from which the electromechanical interval is to be measured. The R wave peak detector 4 responds to the occurrence of the peak of the R wave by enabling a timer 6 which then begins to count from zero. The timer 6 may be any conventional timer and in the preferred embodiment comprises a ramp generator having a capacitor initially at zero charge. Upon detection of the peak of the R wave, the timer 6 permits a constant current to be applied to a capacitor contained therein, the charge on the capacitor and, therefore, the voltage across it increasing linearly. The voltage across the timer capacitor, as a function of time, is shown in FIG. 2E and is governed by the ECG complex of FIG. 2A and the blood pressure pulse wave form of FIG. 2B. That is the ramp voltage begins to increase from zero at the peak of the R wave and stops increasing at the peak of the summation pulse.

The actual mechanical blood pressure pulse is detected by any conventional blood pressure transducer device and converted to an electrical signal. In the preferred embodiment, a catheter attached to a strain gauge is used to sense the sharp increase in aortic blood pressure and converts that pressure into an electrical signal the amplitude of which is proportional to the absolute blood pressure. Hence, each blood pressure pulse produces a corresponding electrical pulse.

The electrical blood pressure signal is applied to a high pass filter 8 in order to eliminate the DC component associated with absolute blood pressure. The output of the high pass filter 8 is an AC electrical signal representing the variation in blood pressure over time. This signal is applied to a DC restore circuit 10 which offsets the AC component of the electrical blood pressure signal so that it has a baseline or average value substantially at ground. The output of the DC restore circuit 10 is then split into two identical components. The first component is applied to a time delay circuit 12. The time delay circuit 12 may comprise a conventional delay line with a clock and driver circuit 13.

The delayed component of the blood pressure pulse wave is applied to a low pass filter 14, to eliminate high frequency noise, and then inverted and applied to the input of an amplifier 16 having a gain of 2. The inversion may be accomplished in the amplifier 16 by applying the delayed and filtered component to a negative input of the amplifier 16 as will be known to those skilled in the art. The output of the amplifier 16 is shown in FIG. 2C.

The second component of the blood pressure pulse waveform out of the DC restore circuit 10 is applied to a low pass filter 18. Filters 14 and 18 are identical so that the phase difference between the two components of the blood pressure signal remains constant. The output of the lowpass filter 18 is shown in FIG. 2B.

Both components of the blood pressure pulse waveform are then applied to a common node 20 where they are added and the resultant sum is applied to the input of a pressure peak detector 22. The summation waveform applied to the pressure peak detector 22 is shown in FIG. 2D.

When the pressure peak detector 22 senses that the summation waveform has reached a peak, it provides output signals to a sample and hold circuit 24 and a timer reset circuit 26. The sample and hold circuit 24 responds to the output of the pressure peak detector 22 by sampling the voltage value of the capacitor in the timer 6 which is proportional to the elapsed time from the peak R of the R wave to the peak $P_s$ of the blood pressure summation wave. The reset circuit 26 then causes the timer 6 to reset to zero by discharging the capacitor in the timer 6. The timer 6 is again actuated in response with the next R wave peak as detected by the R wave peak detector 4.

The output of the sample and hold circuit 24 is then applied to a subtractor circuit 28 where a voltage proportional to the time interval $\theta$ by which the first component of the blood pressure waveform was delayed is subtracted from the time difference between the peaks R and $P_s$ of the R wave and summation wave respectively to yield a voltage proportional to the electromechanical interval. Referring to FIG. 3A, a polarity detector 23 may be substituted for the peak detector 22 in which case, as can be seen from FIGS. 1B and 2D, a voltage proportional to the time delay $\theta$ which is also a function of the gain of the amplifier 16 is subtracted from the time difference between the peak R of the R wave and the zero crossing of the summation wave to yield a voltage proportional to the electromechanical interval. From FIGS. 1A and 1B it can be seen that $\alpha = \theta$ and $\beta = K\theta/K-1$ where K is the magnitude of the negative gain of the amplifier 16. In the example shown in FIG. 1A, K = 2.

Figure 4A:
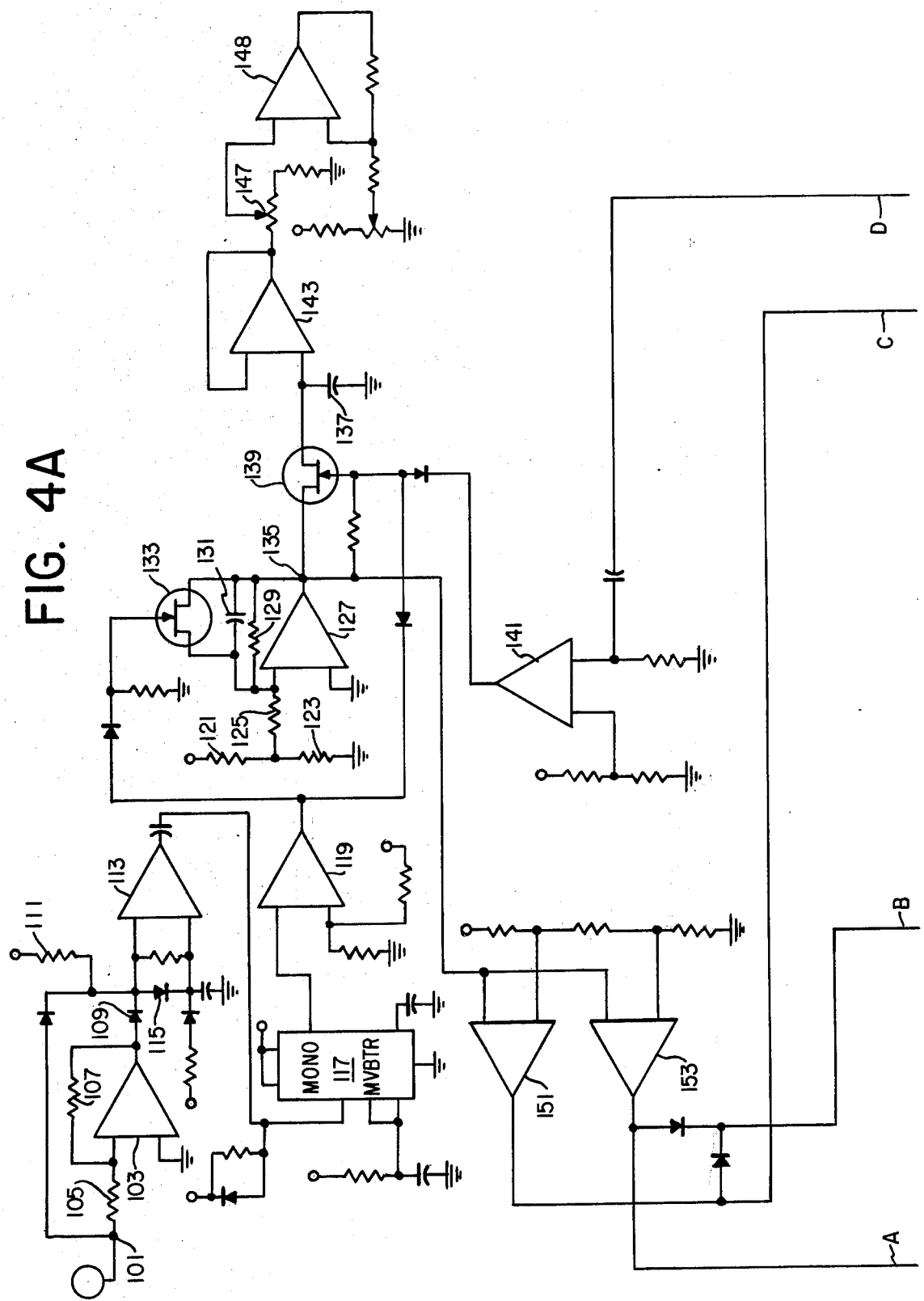
FIGS. 4A, 4B and 4C are schematic drawings of the circuitry employed in the apparatus used to determine electromechanical interval.
Figure 4B:
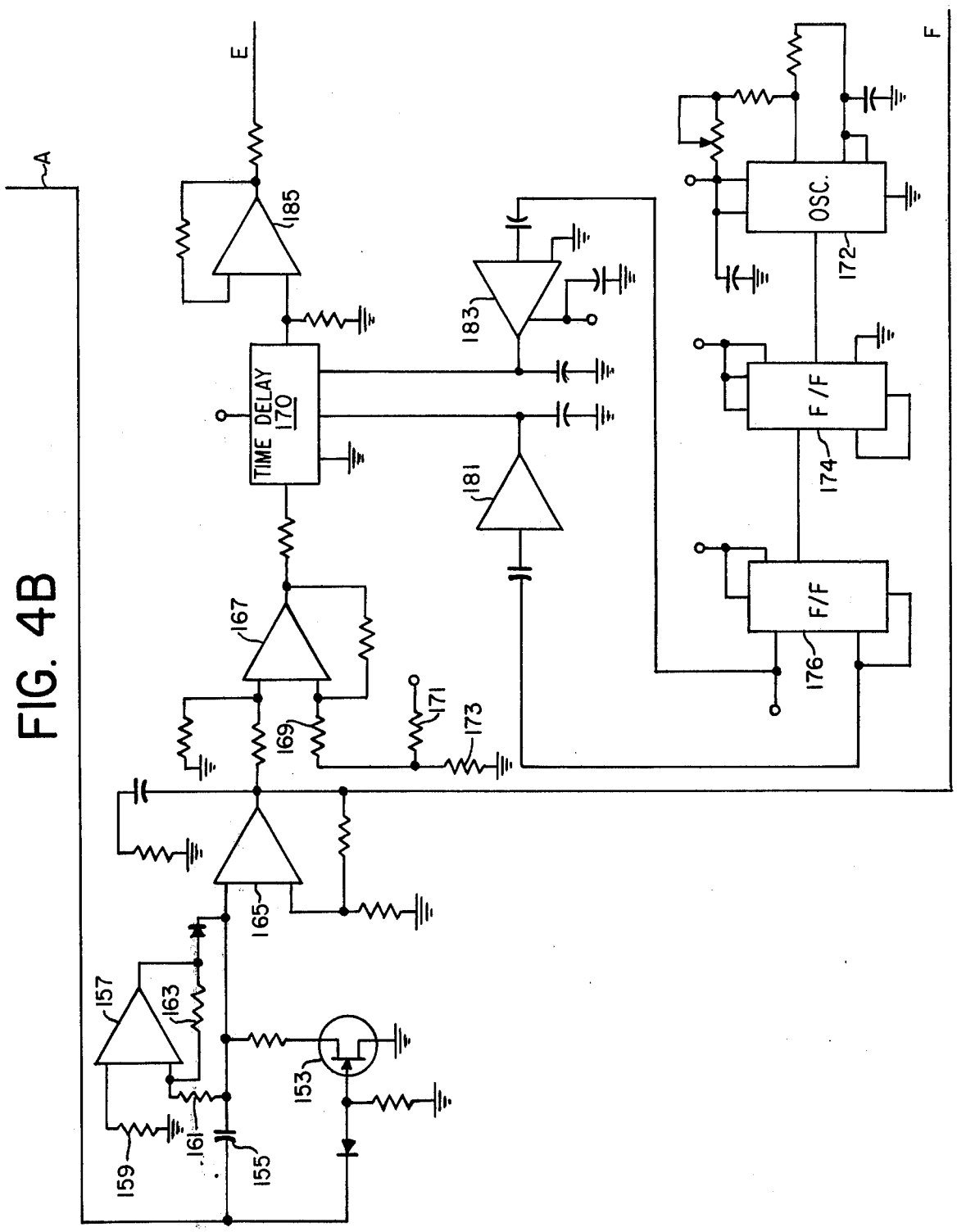
Figure 4C:
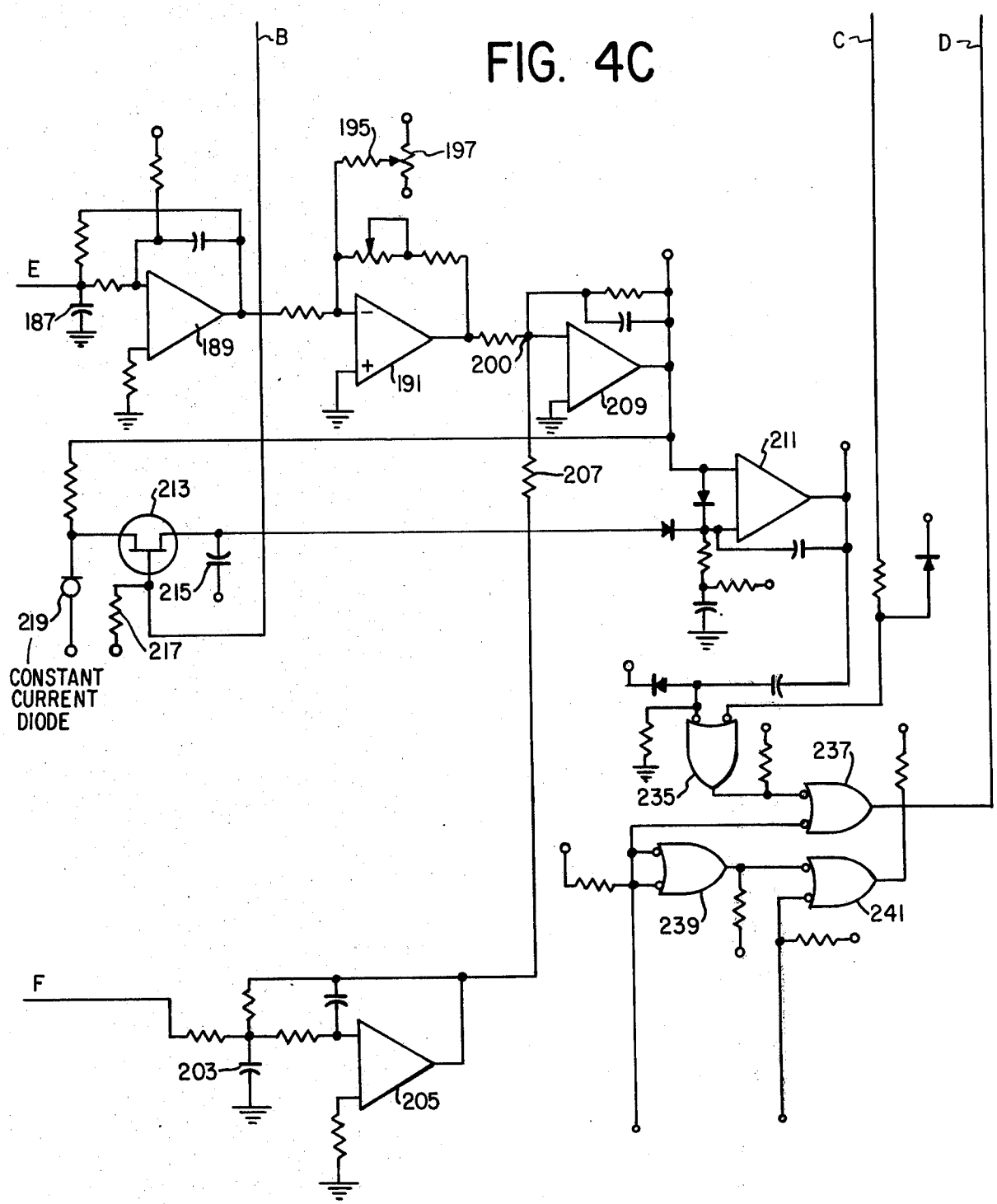

A circuit for accomplishing the aforementioned functions is illustrated in FIGS. 4A, 4B and 4C. The operation of the circuit will be known to those familiar with the art and will only be briefly described.

Referring to FIG. 4A, the ECG input is applied at node 101 which is the input of a fullwave amplifier circuit. The integrated circuit amplifier 103 is wired with identical input and feedback resistors 105 and 107 for a gain of unity. The output of the amplifier circuit 103 is applied to a diode 109 which is biased at 15 volts below ground potential via the resistor 111. The output of the amplifier 109 is applied to a comparator 113 across a diode 115 which is back-biased by a positive 15 volts. The comparator 113 detects the highest peak of the ECG input, that is, the R wave. When the R wave peak is detected, the output of the two-state comparator 113 shifts from a low to a high state actuating a monostable multivibrator 117.

The output of the monostable multivibrator 117 is applied through a level shift circuit 119 to a timer circuit which comprises a ramp generator. The timer circuit includes resistors 121, 123 and 125, amplifier 127, feedback resistor 129 and feedback capacitor 131. A field effect transistor 133 is connected across the capacitor 131 with its gate receiving the output of the level shift circuit 119. When the field effect transistor 133 receives an actuating command from the ECG peak detector 250 ms after the ECG as, hereinafter described, it shorts out capacitor 131 thereby discharging it and resetting the timer to zero.

The output of the ramp generator at node 135 is applied to capacitor 137 in the sample and hold circuit via the field effect transistor 139 which closes momentarily upon receipt of an interrogate pulse from the comparator 141 in response to the detection of the pressure peak. A high impedance buffer amplifier 143 prevents the capacitor 137, wherein the sampled timer voltage is held, from discharging. The sampled timer voltage is applied to a subtractor circuit which includes amplifier 148 with resistors wired for varying its gain. The voltage in the sample and hold capacitor 137 is applied through the buffer amplifier 143 to the subtractor amplifier 148 via the wiper arm of a potentiometer 147. The subtractor circuit amplifier 148 is wired with variable resistors as shown in the figure to permit the time delay incorporated into the blood pressure circuit, hereinafter described, to be subtracted from the final timer reading so that the electromechanical interval may be determined.

The mechanical blood pressure wave may be converted to an electrical signal by a strain gauge transducer and associated circuit, not shown, the output of which, at any given time, has an amplitude proportional to a subject's blood pressure. In order to prevent spurious signals from influencing the results of the EMI measurement, the blood pressure input circuitry and pressure peak detection circuitry are disabled until actuated by pulses from comparators 151 and 153 50 milliseconds after the R wave of the ECG is detected. Typical EMI's are on the order of one hundred milliseconds and by disabling the system for the first 50 milliseconds following the R wave, valid data is preserved while spurious signals are kept from entering the system.

Referring now to FIG. 4B the blood pressure pulse input is applied to a capacitor 155 which serves as a high pass filter eliminating the DC component of the blood pressure wave. A DC restore circuit comprising amplifier 157 and associated resistors 159, 161 and 163 restores a DC component to the blood pressure waveform to keep the base line or average of the blood pressure waveform at about ground level. The output of the DC restore circuit is applied to an amplifier 165 having a gain of 2 and then to a level shift circuit comprising amplifier 167 and level shift offset resistors 169, 171 and 173 to which a positive 15 volts is applied. This shifts the base line of the blood pressure waveform from ground potential to a level of about −8 volts. The level shift amplifier 167 has a gain of unity.

The output of the level shift amplifier 167 is then applied to a time delay circuit 170 which is controlled by a conventional clock and driver circuit including oscillator 172 and flip-flops 174 and 176. The outputs of the dividers are applied to the delay circuit 170 through the driver circuits 181 and 183. The output of the delay circuit 170 is applied to a buffer amplifier 185 and then (in FIG. 4C) to capacitor 187 which acts as a low pass filter to remove the carrier from the blood pressure waveform. The buffer amplifier 185 is wired to reverse the polarity of the blood pressure waveform applied to it thus acting as an inverter.

The envelope of the blood pressure waveform is then applied to amplifier 189 having a gain of unity and amplifier 191 which has a gain of 2. The negative input to the amplifier 191 at which the blood pressure waveform is applied is tied via a resistor 195 to the wiper arm of the potentiometer 197 to provide the necessary adjustment for cancelling the previously introduced voltage offsets.

The blood pressure waveform inverted and multiplied by a gain of 2 is then applied to the node 200 where it is summed with the original unmodified blood pressure signal, taken from the output of the amplifier 165. The unmodified blood pressure signal is applied to a low pass filter comprising a capacitor 203 which is identical to the low pass filter comprising capacitor 187 to prevent any phase shifts introduced by the filters from adversely affecting the EMI computation. Thus any phase shift imparted by the low pass filters will be equally applied to the original blood pressure waveform and the inverted one thereby leaving $\theta$, the intended time delay between the two waveforms, unchanged. The output of the low pass filter circuit, which in addition to capacitor 203 includes amplifier 205, is applied to the summation node 200 through the resistor 207. Amplifiers 189, and 205, are identical as are their associated resistors and capacitors. The sum of the signals is then amplified to a gain of 22 by amplifier 209 and applied to a peak detector circuit comprising a comparator 211 which is biased by the output of a peak detector threshold circuit. The peak detector threshold circuit comprises field effect transistor 213, capacitor 215 to which a 5 volts DC bias is applied, resistor 217 through which −15 volts is applied, and constant current diode 219.

When the sum (FIG. 2D) of the unmodified blood pressure signal (FIG. 2B) and the inverted, amplified and time delayed component (FIG. 2C) reaches a peak, the comparator 211 switches to a high state activating a logic network comprising gates 235, 237, 239 and 241. A pulse is then sent to the comparator 141 which in turn causes an interrogate pulse to be generated causing the ramp voltage stored in the timer to be sampled. The interrogate pulse closes the field effect transistor 139 momentarily, as previously described, thereby permitting the capacitor 137 to charge up to the instantaneous value of the ramp voltage stored in capacitor 131.

The time of detection of the peak $P_s$ of the summed waveform (FIG. 2D) is equal to the electromechanical interval plus the time delay $\theta$ imparted by time delay circuit 170. The time delay $\theta$ is subtracted from the result of this summation, the difference being the electromechanical interval.

It will be appreciated that the heretofore described circuits may be varied by substitution of different components and different component configurations to perform like functions by those familiar with the art. The circuit description is intended only to disclose one preferred embodiment of the invention which may take on many forms and the scope of which is to be limited only by the following claims.

What is claimed is:

1. Apparatus for determining the time of onset of an electrical pulse measured from a reference time comprising:
    means for producing from each said electrical pulse an identical corresponding respective pulse;
    means for shifting the phase of said corresponding pulse with respect to said electrical pulse by a predetermined time;
    means for inverting and amplifying said phase shifted corresponding pulse;
    means for combining said electrical pulse with said corresponding amplified, inverted and phase shifted respective pulse to form a combined pulse;
    timer actuating means operative at said reference time;
    a timer responsive to said actuating means and to a predetermined characteristic of said combined pulse for producing a first signal having a characteristic with a magnitude related to the time of occurrence of said combined pulse characteristic measured from said reference time;
    means for producing a second signal having a characteristic with a magnitude related to said predetermined phase shift time; and
    means for combining said first and second signals to form a third signal having a characteristic with a magnitude related to the difference in magnitudes of said respective characteristics of said first and second signals, said third signal characteristic magnitude being related to said onset time.

2. Apparatus according to claim 1 wherein said predetermined characteristic is the peak of said combined pulse.

3. Apparatus according to claim 1 wherein said predetermined characteristic is the point of change in voltage polarity of said combined pulse.

4. Apparatus for determining the time of onset of an electrical pulse comprising:
    means for splitting said electrical pulse into respective first and second pulses with waveforms identical to that of said electrical pulse;
    means for delaying said first pulse for a constant time period;
    means for inverting and amplifying said delayed first pulse;
    means for adding said delayed inverted and amplified first pulse and said second pulse to form a summation pulse;
    means for detecting a predetermined characteristic of said summation pulse;
    timing means responsive to said detection means for indicating the time at which said predetermined characteristic occurs,
    means for actuating said timing means; and
    means for subtracting said constant time period from said predetermined characteristic occurrence time, the output of said subtracting means being proportional to the time of onset of said pulses.

5. Apparatus according to claim 4 wherein said actuating means comprises means for detecting the occurrence of an event, said timing means being actuated in response to said event for measuring said onset time from said event.

6. Apparatus according to claim 4 wherein said predetermined characteristic is the peak of said summation pulse.

7. Apparatus according to claim 6 further comprising means responsive to said summation pulse peak detecting means for resetting said timing means for a new measurement.

8. Apparatus according to claim 4 wherein said predetermined characteristic is the point of change in voltage polarity of said summation pulse.

9. A method of determining the time of onset of electrical pulses having varying amplitudes and slopes relative to a reference time comprising:
    actuating a timer to measure the time elapsed from said reference time;
    splitting each of said electrical pulses into respective first and second identical pulses;
    delaying said first pulse for a constant time period;
    amplifying and inverting said delayed first pulse;
    adding said amplified and inverted first pulse to said second pulse to form a summation pulse;
    detecting the occurrence of a predetermined characteristic of said summation pulse;
    determining from said timer the time elapsed from said reference time at said occurrence; and
    subtracting from said elapsed time at said occurrence said constant time period.

10. A method according to claim 9 wherein said predetermined characteristic is the peak of said summation pulse.

11. A method according to claim 9 wherein said predetermined characteristic is the point of change in voltage polarity of said summation pulse.

12. In an apparatus for determining the time interval between one electrical pulse indicating a first event and a following electrical pulse indicating a second event having a timer which begins measuring time in response to said one pulse and ceases measuring time upon onset of said following pulse, the improvement which comprises:
    means for splitting said following pulse into respective first and second identical pulses, means for delaying said first pulse for a constant time period, means for inverting and amplifying said delayed first pulse, means for summing said delayed inverted and amplified first pulse and said second pulse to form a summation pulse, means for detecting a predetermined characteristic of said summation pulse, means responsive to said detecting means for storing the measurement in said timer, and means for subtracting from the measurement in said storing means, said constant time period.

13. Apparatus according to claim 12 wherein said predetermined characteristic is the point of change in voltage polarity of said summation pulse.

14. Apparatus according to claim 12 wherein said predetermined characteristic is the peak of said summation pulse.

15. Apparatus for determining the electromechanical time interval between the myocardial electrical impulse transmitted to the heart of a subject and the onset of the absolute blood pressure pulse resulting from the heartbeat induced by the myocardial impulse comprising:

means for producing an electrical waveform symmetrical to the waveform of said absolute blood pressure pulse, means for producing from said electrical waveform first and second signals having identical waveforms symmetrical thereto, means for shifting the phase of said first signal by a predetermined time, means for inverting and amplifying said phase shifted signal to form a third signal, means for combining said second and third signals to form a fourth signal, timing means for detecting the time of occurrence of a predetermined characteristic of said fourth signal, said timing means including actuating means responsive to said myocardial electrical impulse to measure time therefrom and produce a fifth signal having a characteristic with a magnitude related to the time from said myocardial impulse to said time of occurrence, means for producing a sixth signal with a characteristic having a magnitude related to said phase shift time, and means for combining said fifth and sixth signals to form a seventh signal having a characteristic with a magnitude related to the difference in magnitudes of said respective characteristics of said fifth and sixth signals, said seventh signal characteristic magnitude being related to said electromechanical interval.

16. Apparatus for determining the electromechanical time interval between the myocardial electrical impulse transmitted to the heart of a subject and the onset of an electrical signal waveform representative of the absolute blood pressure pulse resulting from the heartbeat induced by the myocardial impulse comprising:

means for producing from said electrical signal first and second signals identical thereto, means for delaying said first signal by a predetermined amount of time to yield a delayed signal, means for inverting and amplifying said delayed signal, means for adding said inverted and amplified delayed signal to said second signal to form a resultant signal, means for detecting the peak of said resultant signal, timing means for measuring elapsed time, said timing means being responsive to said myocardial electrical impulse for beginning said measurement and responsive to said peak detecting means for terminating said measurement, and means for subtracting from said terminated count said predetermined amount of time.

17. Apparatus according to claim 16 further comprising means responsive to said myocardial electrical impulse for resetting the measurement in said timing means to zero.

* * * * *